(12) United States Patent
Hunt

(10) Patent No.: US 11,000,609 B2
(45) Date of Patent: May 11, 2021

(54) SYSTEMS AND APPARATUS FOR ULTRAVIOLET LIGHT DISINFECTION

(71) Applicant: CLASS 1 INC., Cambridge (CA)

(72) Inventor: Barry Hunt, Cambridge (CA)

(73) Assignee: CLASS 1 INC., Cambridge (CA)

( * ) Notice: Subject to any disclaimer, the term of this patent is extended or adjusted under 35 U.S.C. 154(b) by 0 days.

(21) Appl. No.: 15/933,792

(22) Filed: Mar. 23, 2018

(65) Prior Publication Data

US 2018/0272016 A1 Sep. 27, 2018

Related U.S. Application Data

(60) Provisional application No. 62/475,393, filed on Mar. 23, 2017.

(51) Int. Cl.
*A61L 2/10* (2006.01)
*F21V 29/60* (2015.01)
*G02B 5/08* (2006.01)

(52) U.S. Cl.
CPC .............. *A61L 2/10* (2013.01); *F21V 29/60* (2015.01); *G02B 5/0891* (2013.01)

(58) Field of Classification Search
None
See application file for complete search history.

(56) References Cited

U.S. PATENT DOCUMENTS

| | | | | |
|---|---|---|---|---|
| 4,434,562 A * | 3/1984 | Bubley | ............... | B41F 23/0409 34/278 |
| 4,563,589 A * | 1/1986 | Scheffer | ............... | H05B 3/0066 250/504 R |
| 4,591,724 A * | 5/1986 | Fuse | ............... | B01J 19/123 250/454.11 |
| 4,707,116 A * | 11/1987 | Newiger | ............... | G03F 7/2002 355/113 |
| 4,786,812 A * | 11/1988 | Humphreys | ............... | A61L 9/20 250/455.11 |
| 5,099,586 A * | 3/1992 | Anderson | ............... | F26B 3/283 34/275 |
| 5,505,912 A * | 4/1996 | Hallett | ............... | A61L 2/10 422/186.3 |
| 5,932,886 A * | 8/1999 | Arai | ............... | B01J 19/123 250/504 R |
| 6,897,460 B2 * | 5/2005 | Kobayashi | ............... | A61L 2/10 250/494.1 |
| 6,981,782 B2 * | 1/2006 | Kai | ............... | F21V 29/00 348/E5.137 |
| 9,099,213 B2 * | 8/2015 | Wilson | ............... | G21K 5/00 |

(Continued)

FOREIGN PATENT DOCUMENTS

| | | | | | |
|---|---|---|---|---|---|
| JP | 57045338 A | * | 3/1982 | ............ | B01J 19/123 |
| JP | 57045338 A | * | 3/1982 | ............ | B01J 19/123 |

*Primary Examiner* — Andrew Smyth
(74) *Attorney, Agent, or Firm* — Dinsmore & Shohl LLP

(57) ABSTRACT

A disinfection system is provided herein. The disinfection system includes an UV light source to generate UV light and a housing supporting the UV light source. The housing includes a fan and a shield having a body partially surrounding the UV light source. The body has an inner surface sized and shaped to reflect the UV light from the UV light source. The body defines at least one hole configured to receive air flow from the fan and direct the air flow to contact the UV light source to control a temperature of the UV light source.

16 Claims, 15 Drawing Sheets

(56) References Cited

U.S. PATENT DOCUMENTS

| | | | |
|---|---|---|---|
| 9,265,174 B2* | 2/2016 | Shostak | H05K 7/20136 |
| 2004/0149936 A1* | 8/2004 | Schweitzer | B05D 3/067 |
| | | | 250/504 R |
| 2005/0167611 A1* | 8/2005 | Elsegood | C02F 1/325 |
| | | | 250/435 |
| 2010/0092346 A1* | 4/2010 | Jeon | A61L 9/205 |
| | | | 422/122 |
| 2014/0292970 A1* | 10/2014 | Rae | B41F 23/0483 |
| | | | 347/102 |
| 2017/0199463 A1* | 7/2017 | Owada | G03F 7/70933 |

* cited by examiner

SYSTEMS AND APPARATUS FOR ULTRAVIOLET LIGHT DISINFECTION

TECHNICAL FIELD

The following relates to systems and apparatus for disinfection, and more specifically to systems and apparatus for UV light disinfection of surfaces.

BACKGROUND

Disinfecting surfaces, such as those found in patient areas, can be performed by exposing the hard surfaces to ultraviolet C (UVC) light. UVC light is a low wavelength subtype of UV light that is known to be harmful to micro-organisms such as bacteria, viruses and fungi. It is believed that the short wavelength radiation destroys organisms at a microorganic level by destroying their nucleic acids, thereby disrupting the organisms' DNA. Once the DNA chain is disrupted, the organisms are unable to cause infection.

There are several advantages to utilizing UV light for disinfecting surfaces. First, generating UV light only requires electricity. UV light does not require the use of any potentially hazardous chemicals that could present storage challenges or potentially leave a residue on a disinfected surface. UV light also does not require a drying time and requires little manpower and skill to apply. Further, UV light generally uses long-lasting UV light sources that do not require significant management and/or maintenance.

One limitation to using UV light for disinfecting surfaces is that UV light generated by the aforementioned UV light sources can vary in intensity based on the temperature of the UV light source. Generally, as the temperature of a UV light source increases during usage, the intensity of the UV light generated by the light source decreases. This can be particularly significant for UV light sources mounted on or within a housing and/or for UV light sources that utilize a reflecting surface to disperse UV light upon generation. UV light sources in these configurations can increase in temperature shortly after being energized, thereby leading to generation of low intensity UV light and inefficient disinfection.

SUMMARY

According to one aspect, a shield for reflecting UV light from a UV light source is provided. The shield has a body partially surrounding the UV light source and an inner surface sized and shaped to reflect the UV light from the UV light source. The body defines a hole configured to receive air flow from a fan and direct the air flow to impinge the UV light source to control a temperature of the UV light source.

According to another aspect, a housing for supporting a UV light source is provided. The housing has a fan and a shield fluidly coupled to the fan. The shield has a body partially surrounding the UV light source and an inner surface sized and shaped to reflect the UV light from the UV light source. The body defines a hole configured to receive air flow from the fan and direct the air flow to impinge the UV light source to control a temperature of the UV light source.

According to another aspect, an ultraviolet (UV) light disinfection system is provided. The system includes an UV light source to generate UV light and a housing for supporting the UV light source. The housing has a fan and a shield fluidly coupled to the fan. The shield has a body partially surrounding the UV light source and an inner surface sized and shaped to reflect the UV light from the UV light source. The body defines a hole configured to receive air flow from the fan and direct the air flow to impinge the UV light source to control a temperature of the UV light source.

According to another aspect of the shield, the body is an elongate member.

According to another aspect of the shield, the body is curved.

According to another aspect of the shield, the body is semi-circular.

According to another aspect of the shield, the holes are a plurality of holes.

According to another aspect of the shield, the holes are slots.

According to another aspect of the shield, the holes are regularly spaced along a length of the body.

According to another aspect of the shield, the slots are on one side of the body.

According to another aspect of the shield, the body made of is anodized aluminum.

According to another aspect of the shield, the inner surface made of is anodized aluminum.

Additional aspects will be apparent in view of the description which follows. It should be understood however that the detailed description and the specific examples, while indicating preferred embodiments, are given by way of illustration only, since various changes and modifications will become apparent to those skilled in the art from this detailed description.

BRIEF DESCRIPTION OF THE DRAWINGS

The drawings included herewith are for illustrating various examples of articles, methods, and apparatuses of the present specification. In the drawings.

DETAILED DESCRIPTION

Various apparatuses or processes will be described below to provide an example of each claimed embodiment. No embodiment described below limits any claimed embodiment and any claimed embodiment may cover processes or materials that differ from those described below. The claimed embodiments are not limited to materials or processes having all of the features of any one material or process described below or to features common to multiple or all of the materials described below. It is possible that a material or process described below is not covered by any of the claimed embodiments. Any embodiment disclosed below that is not claimed in this document may be the subject matter of another protective instrument, for example, a continuing patent application, and the applicants, inventors or owners do not intend to abandon, disclaim or dedicate to the public any such embodiment by its disclosure in this document.

Figure 1:
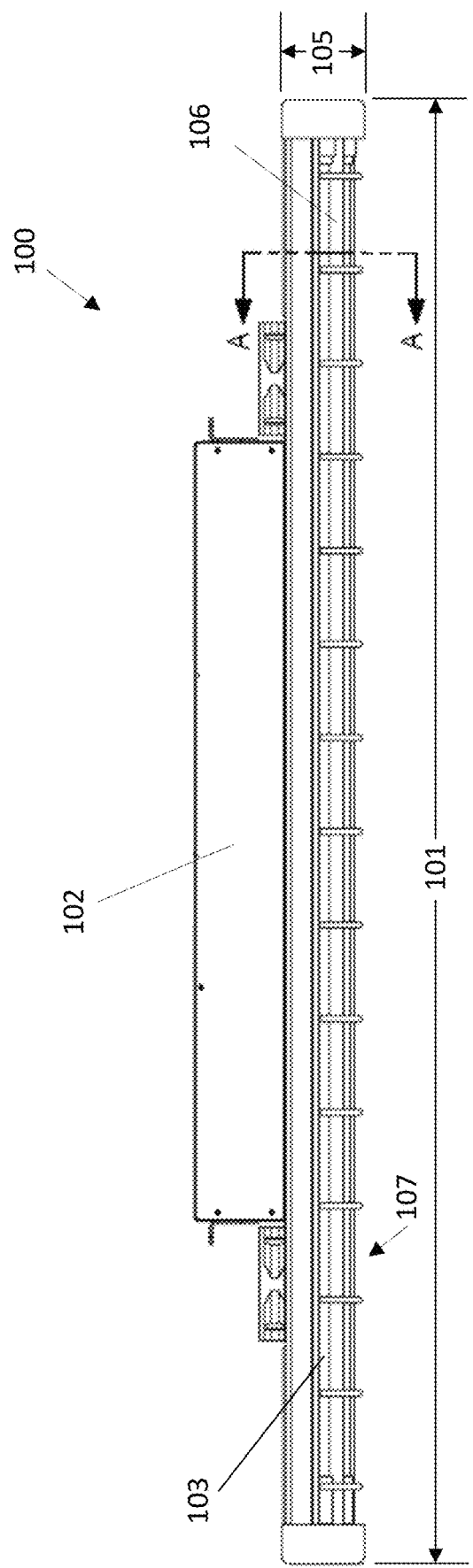
FIG. 1 is a side view of a disinfection system according to one embodiment.

Referring to FIG. 1, illustrated therein is a disinfection system 100 according to one embodiment. The disinfection system 100 comprises a housing 102 to support a light source (e.g. bulb) 106. In some embodiments, housing 102 can support more than one light source 106. For example, in the embodiment of system 100 shown in FIGS. 1-4, housing 102 is shown as supporting four light sources 106 (see specifically FIG. 2). The system 100 is shown upright (e.g. in a horizontal configuration) in FIG. 1. The system 100 can also be utilized in a vertical configuration (not shown).

Housing 102 defines a first cavity 103 having an opening 107. First cavity 103 and opening 107 generally extend along a length 101 and a width 106 of housing 102. First cavity 103 extends inward of housing 102 from opening 107 to provide for housing 102 to receive a light source(s) 106. In one embodiment, first cavity 103 and opening 107 are an elongate cavity and elongate opening, respectively. When a light source(s) 106 is received in first cavity 103 and mounted to housing 102, opening 107 also facilitates transmission (e.g. dispersion) of light generated by the light source(s) 106 out of first cavity 103. Opening 107 is configured so that when a light source(s) 106 is mounted within first cavity 103 of housing 102, opening 107 faces away from light source(s) 106 at a bottom of first cavity 103. Light source(s) 106 can be mounted to housing 102 in any appropriate manner known to one skilled in the art.

In an embodiment, housing 102 is an elongate member having a length 101 greater than its width 106. Housing 102 can be made from any appropriate material.

Light source(s) 106 can also be an elongate member having a length greater than its width. Light source(s) 106 can be any appropriate light source that, upon being energized, generates and transmits light in an outward direction of a wavelength sufficient to disinfect a surface (e.g. to kill or otherwise destroying harmful microorganisms such as bacteria, viruses and the like). In one embodiment, light source 106 may generate and transmit UV light. In another embodiment, light source 106 may generate and transmit UVC light where UV-C light is UV light in the wavelength region of 100-280 nm. Light source(s) 106 can be used to sterilize an environment outside of housing 102. Examples of such light sources include but are not limited to, mercury vapor lamps, fluorescent lamps, and metal halide lamps, and combinations of these and other sources.

Figure 3:
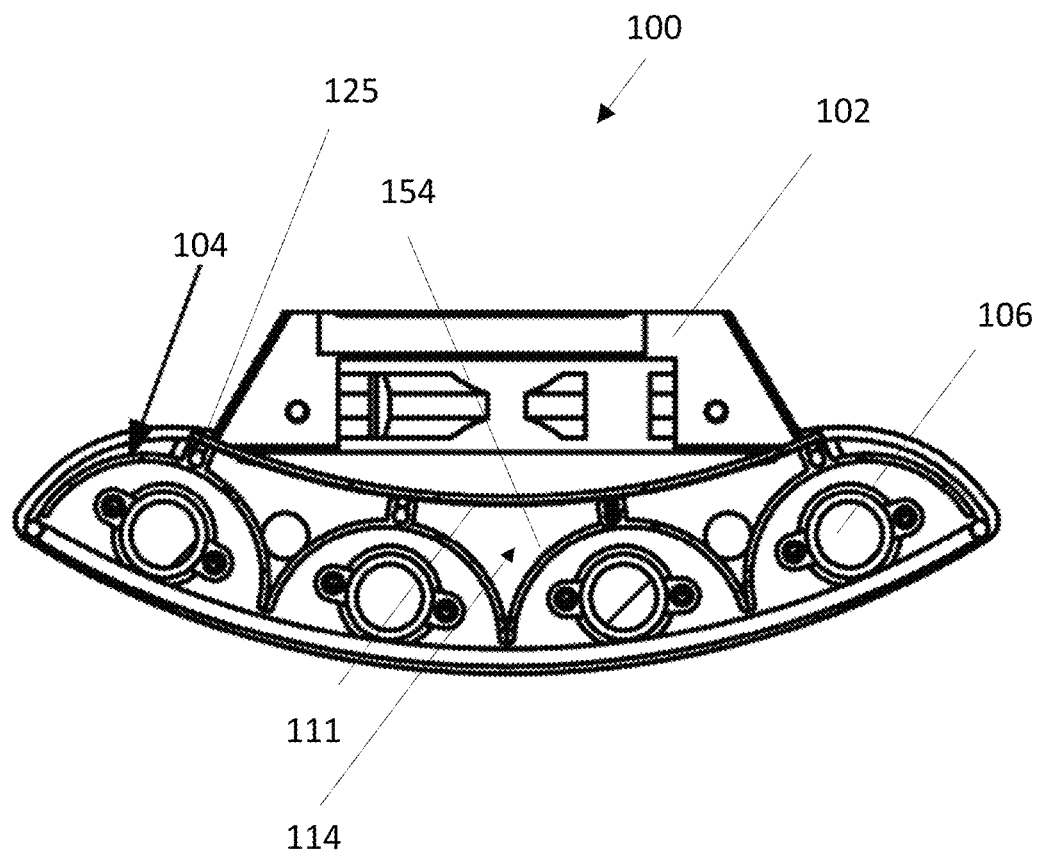
FIG. 3 is a cross-sectional view of the disinfection system of FIG. 1 along line A-A.

System 100 can further comprise a shield 104. Shield 104 can reflect light generated by the light source(s) 106 to facilitate transmission (e.g. dispersion) of light generated by the light source(s) 106 out of housing 102. Referring to FIG. 3, shield 104 is mountable to housing 102. Shield 104 can be mounted to housing 102. As shown in FIG. 3, shield 104 comprises a channel 125 extending along a length 180 of shield 104. In this embodiment, a coupling agent (e.g. a screw, bolt, or the like, not shown) can be inserted through a top surface 111 of housing 102 into channel 125 to mount shield 104 to housing 102. In another embodiment, shield 104 can be mounted to housing 102 using any appropriate technique known to a skilled person in the art. In another embodiment, shield 104 can be integrally formed with housing 102.

When shield 104 is mounted to housing 102, a second cavity 114 defined by outer surface 154 of shield 104 and an inner surface 111 of housing 102 is formed. Second cavity 114 generally extends along a length 101 of housing 102 and is opposed to opening 107 and light source(s) 106.

Housing 102 further comprises at least one fan 108. Fan 108 can pull air from outside of housing 102 and direct air into housing 102. For example, in one configuration, fan 108 can be positioned within housing 102 to pull air from outside housing 102 into second cavity 114 of housing 102 to be directed towards light source(s) 106.

Accordingly, second cavity 114 can be fluidly coupled with fan 108 to receive air flow from fan 108 and direct air flow along the length 101 and/or the width 105 of housing 102. In this respect, second cavity 114 can provide a conduit for air flow to move from fan 108 along the length 101 and width 105 of housing 102 adjacent to light source(s) 106. It should be noted that more than one second cavity 114 can be formed within housing 102. In one embodiment, second cavity 114 is defined by outer surface 154 of shield 104 and an inner surface 111 of housing 102 and ends plates (not shown) of housing 102 (see FIG. 7).

Figure 4:
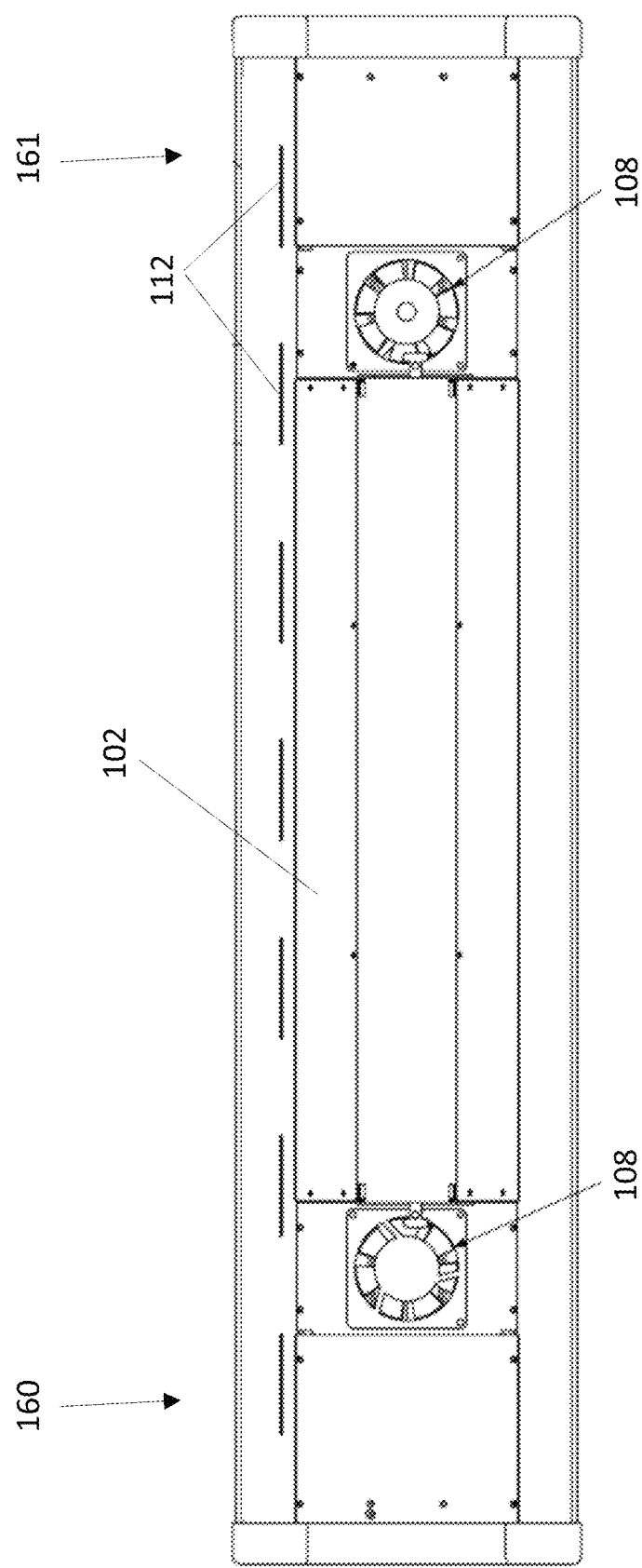
FIG. 4 is a top view of the disinfection system of FIG. 1.

As shown in FIG. 4, the embodiment of system 100 shown in FIGS. 1-4 comprises two fans 108. In this embodiment, one fan 108 is positioned at a first end 160 of housing 102 to provide for air flow through second cavity 114 and one fan 108 is positioned at a second end 161 to provide for air flow through second cavity 114. Housing 102 may also comprise more than two fans.

In another embodiment, housing 102 can comprise ducts positioned within second cavity 114 when shield 104 is mounted to housing 102. Ducts can be used to direct the air flow from the fan(s) 108 along the length 101 and the width 105 of housing 102.

Figure 2:
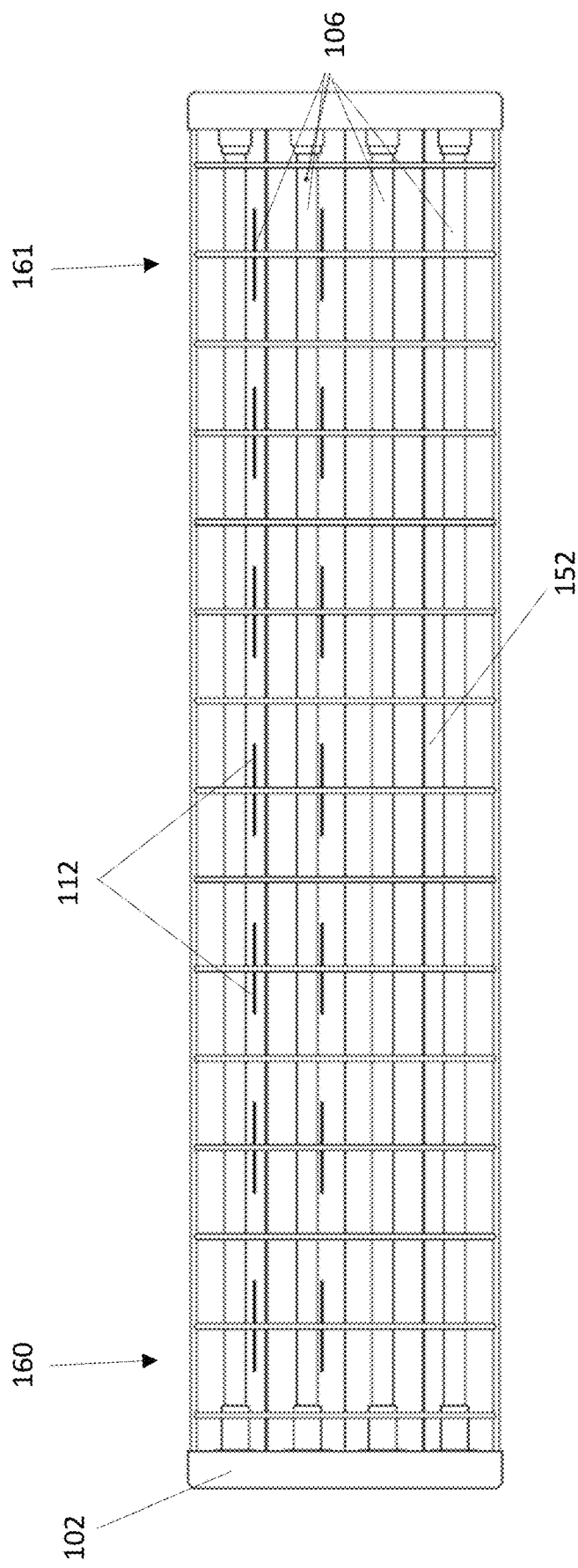
FIG. 2 is a is a bottom view of the disinfection system of FIG. 1.

As shown in FIGS. 2 and 3, each of the four light sources 106 of system 100 has a corresponding shield 104. Each shield 104 reflects light generated by and transmitted from its respective light source 106. In one embodiment, each shield 104 reflects light generated by and transmitted from its respective light source 106 through opening 107 of housing 102. In another embodiment, a shield 104 can be provided to reflect light generated by and transmitted from more than one light source 106.

Figure 7:
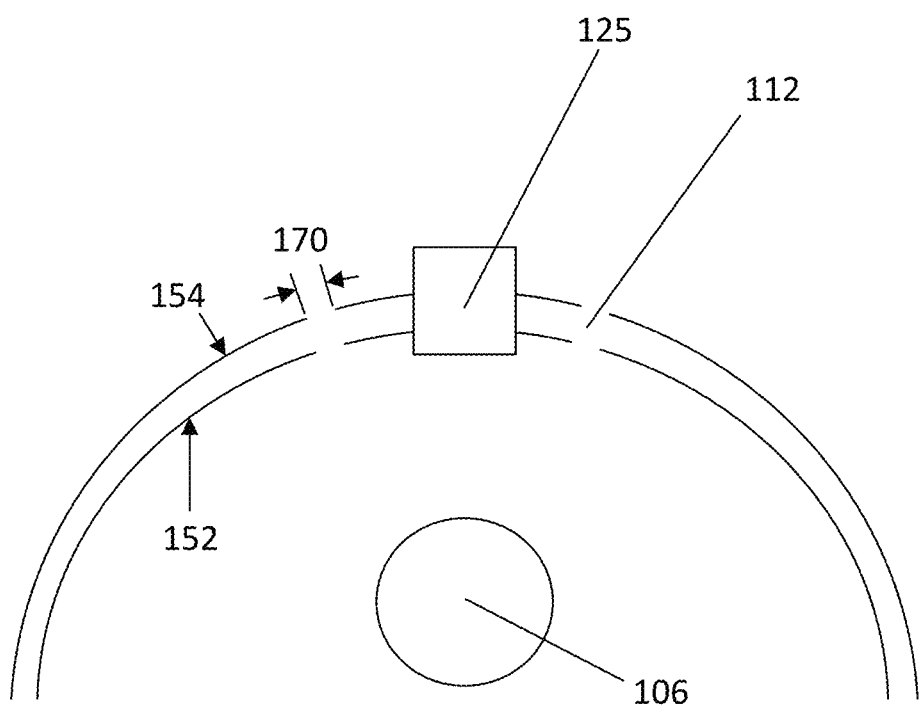
FIG. 7 is a schematic diagram of a cross-sectional view of the shield of FIG. 5 with a light source.

Shield 104 has a body 150 having an inner surface 152, an outer surface 154 and at least one hole 112 traversing the shield 104 from the inner surface 152 to the outer surface 154 (see also FIG. 7).

Inner surface 152 is sized and shaped to reflect light emitted by the light source(s) 106. To reflect light generated by and transmitted from its respective light source 106, shield 104 partially surrounds respective light source 106. Herein, "partially surrounds" refers to at least a portion of shield 104 being positioned to be spaced apart from a corresponding light source 106 to reflect light generated by light source 106. In one embodiment, a portion of shield 104 partially surrounds light source 106 such that light reflected off of shield 104 travels in a direction towards opening 107. In another embodiment, light generated by and transmitted from light source 106 in a direction towards shield 104 can reflect off of an inner surface 152 of shield 104 and be directed through opening 107. In the embodiments shown in the figures, shield 104 is positioned between light source 106 and second cavity 114 of housing 102. The shape of the inner surface 152 and the position of light source(s) 106 with respect to inner surface 152 are such that the illumination pattern of light after reflectance by the inner surface 152 is 180 degrees or more, thereby facilitating the system 100 to provide disinfection to a wide area.

Figure 5:
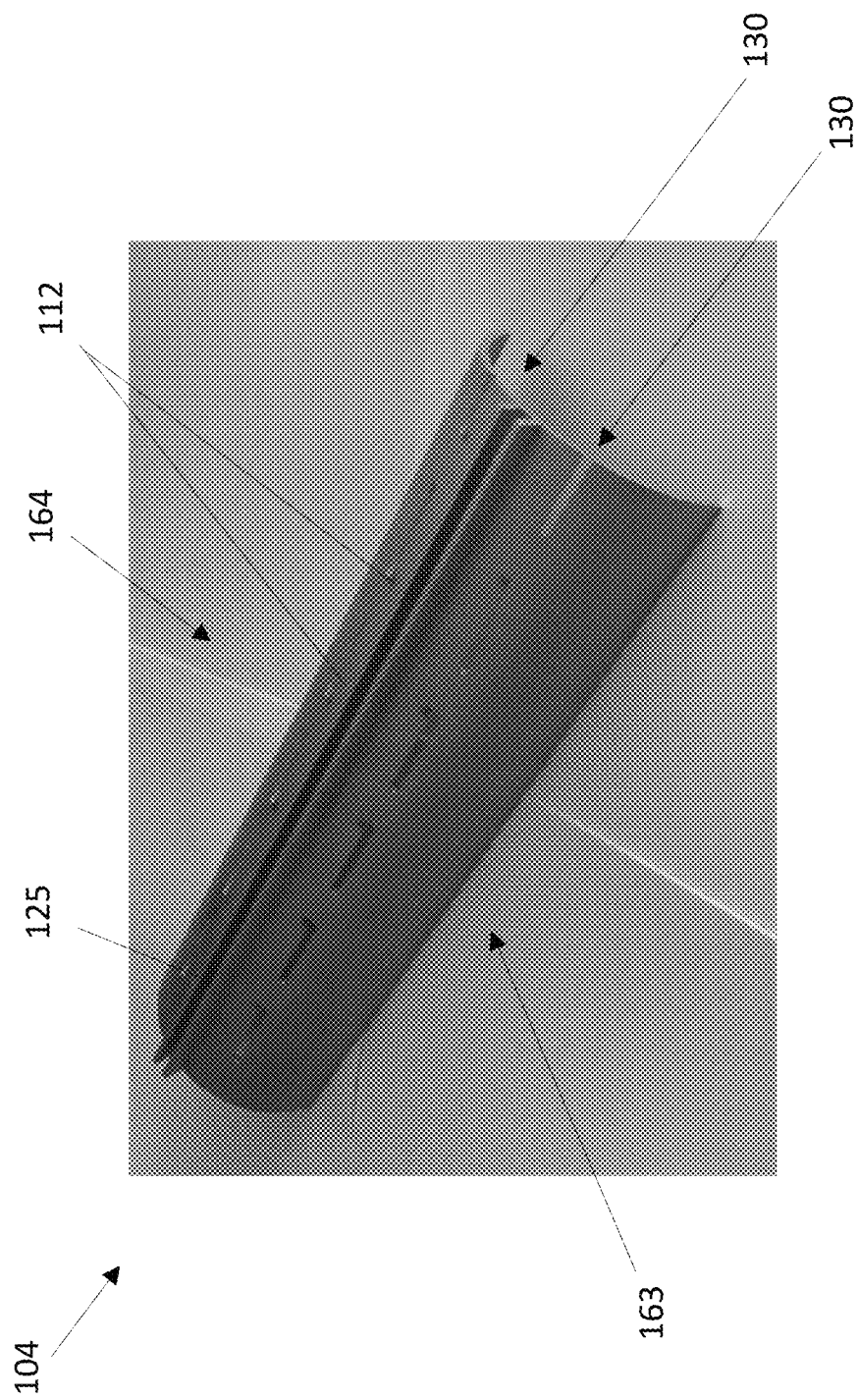
FIG. 5 is perspective view of a shield according to one embodiment.
Figure 6:
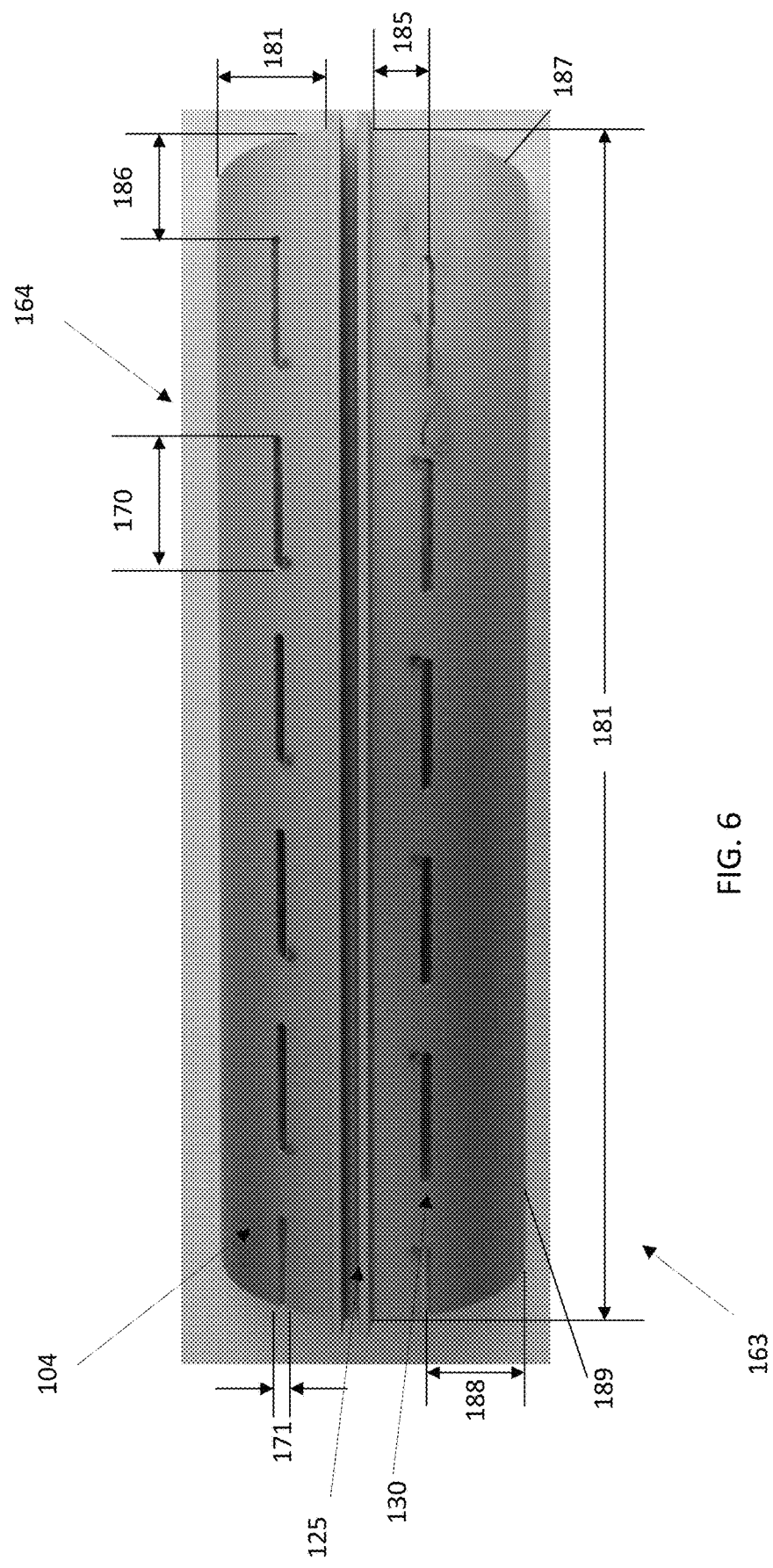
FIG. 6 is a top view of the shield of FIG. 5.

In the embodiments shown in FIGS. 2, 5 and 6, inner surface 152 has a generally concave (e.g. curved) shape and outer surface 154 has a generally convex shape. In one specific example, inner surface 152 has a semi-circular shape and outer surface 154 has a semi-circular shape.

Shield 104 can be made of any appropriate material for reflecting light generated by and transmitted from light source 106. For example, in the embodiments shown in the FIG. 5, shield 104 can be made of aluminum. More specifically, shield 104 can be made of anodized aluminum. Similarly, inner surface 152 can be made of any material appropriate for the reflectance of light. For example, inner surface 152 can be made of (or coated with) aluminum or more specifically anodized aluminum.

As described above, shield 104 defines at least one hole 112. In the embodiments shown in the figures (see FIGS. 5-8), shield 104 defines a plurality of holes 112. Holes 112 couple second cavity 114 and opening 107 such that air moving through second cavity 114 can be directed by holes 112 towards light source 106 and opening 107. Holes 112 can therefore direct air flow from second cavity 114 to contact light source(s) 106. In one embodiment, air contacting light source(s) 106 can be used to control a temperature of light source(s) 106.

FIG. 6 is a top view of the shield 104 of FIG. 5. Holes 112 can be sized and shaped to direct air from second cavity 114 of housing 102 directly onto a surface of light source(s) 106 (e.g. in a direction normal to a surface of light source 106). For example, holes 112 can have a width 170 and a height 171. Width 170 and height 171 of each hole 112 can be adjusted to tune air movement (e.g. speed of air flow, angle of contact between air and light source 106, amount of turbulence in moving air, etc) through the holes 112 and onto or proximate to light source(s) 106. In the embodiment shown in FIGS. 5 and 6, holes 112 include slots (e.g. holes having width 170 greater than height). In another embodiment, holes 112 may have a width 170 of approximately 1" and a height 171 of approximately ⅛". FIG. 7 is a schematic of a cross-sectional view of the shield 104 at least partially surrounding a light source 106.

Figure 8:
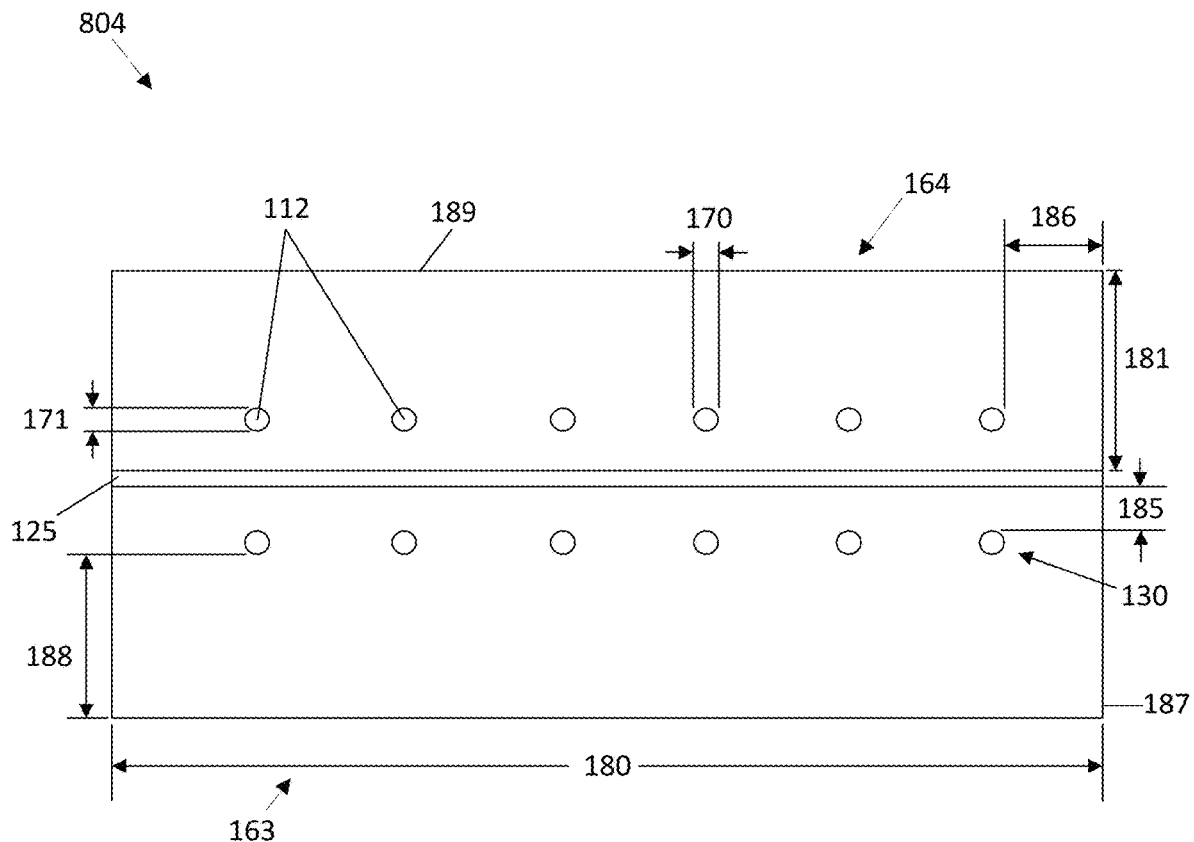
FIG. 8 is a schematic diagram of a top view of a shield having round holes according to another embodiment.

FIG. 8 shows another embodiment of a shield 804 having holes 812 that are round. Hereafter, reference to shield 104 includes reference to shield 804 and reference to holes 112 includes reference to holes 812 holes.

Holes 112 can be sized and shaped to direct air from second cavity 114 of housing 102 to contact a surface of light source(s) 106 such that the air flow forms a 90° angle with the surface of the light source. In another embodiment, holes 112 can be sized and shaped to direct air from second cavity 114 of housing 102 to contact a surface of light source(s) 106 such that the air flow forms an angle other than a 90° angle. In another embodiment, holes 112 can be sized and shaped to direct air from second cavity 114 of housing 102 around (e.g. to not directly contact) light source(s) 106. In another embodiment, the holes 112 can be regularly spaced along a length 180 of shield 104 to form a row 130 of holes 112.

Holes 112 can be also be positioned on shield 104 to tune various characteristics of the air flow including but not limited to velocity, direction and profile through the holes 112. In one embodiment, holes 112 can be positioned along a length 180 of shield 104 to direct air from second cavity 114 towards light source 104 at various positions along the length of light source(s) 106. Further, holes 112 can be positioned at various positions along a width 181 of shield 104 to direct air from second cavity 114 onto light source(s) 106. In an embodiment, holes 112 can be on one or both of a first side 163 and a second side 164 of shield 104. In another embodiment, one or more row 130 of holes can be positioned a distance 185 from channel 125 on of shield 104. In another embodiment, one or more row 130 of holes 112 can be positioned a distance 186 from first edge 187 on first side 163 and/or second side 164 of shield 104. In another embodiment, one or more row 130 of holes can be positioned a distance 188 from second edge 189 on a first side 163 and second side 164 of shield 104. In another embodiment, holes 112 can also be positioned on sides 163, 164 of shield 104 in any pattern desired.

Holes 112 can be formed in shield 104 using any appropriate technique. In one example, holes 112 can be laser cut into shield 104.

In one embodiment, fan 108 can be controlled to tune a velocity of the air flow through holes 112. In one embodiment, the velocity of the air flow through holes 112 can tuned within a range from 1 m/s to 100 m/s. In another embodiment, the velocity of the air flow through holes 112 can tuned within a range from 0.2 m/s to 10 m/s. In another embodiment, fan 108 can be controlled to tune a profile of the air flow through holes 112. In one embodiment, fan 108 can be controlled to provide the air flow through holes 112 with a laminar profile. In another embodiment, fan 108 can be controlled to provide the air flow through holes 112 with a turbulent profile.

In one embodiment, system 100 can be coupled to a power source (not shown) to provide power to the light source(s) 106 and the fan 108. In one embodiment, housing 102 can further comprise a controller to control operation of the light source(s) 106 and/or the fan 108. Optionally, a temperature sensor (not shown) may be added to housing 102 to measure the temperature at a position adjacent to the light source(s) 106 and fan 108 can be controlled by the controller based on the temperature readings by the sensor.

In one exemplary configuration, housing 102 can be mounted to a ceiling of a room such that opening 107 is opposed to the ceiling of the room and faces the floor of the room. In such a configuration, system 100 can project light downward from the ceiling and onto the surfaces to be disinfected or maintained at a disinfected state. In another exemplary configuration, housing 102 can be mounted to a wall of a room such that opening 107 is opposed to the wall and faces the contents of the room. In these configurations, activation of the light source(s) 106 generates light that can be both directly transmitted through opening 107 and reflected off of shield 104 to be transmitted through opening 107.

Figure 9:
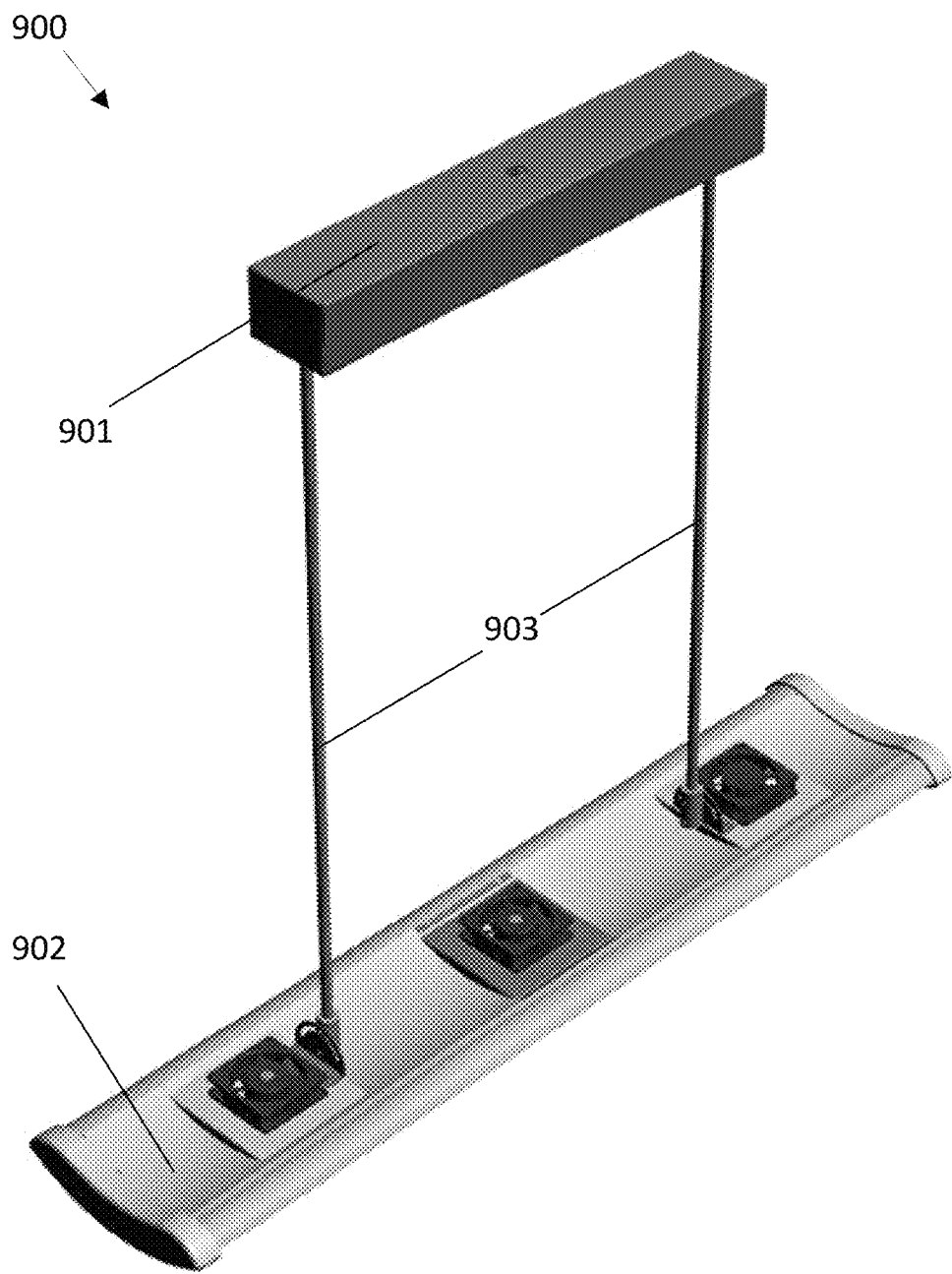
FIG. 9 is a perspective view of a disinfection system with a separate ballast according to another embodiment.

FIG. 9 shows an embodiment of a disinfection system 900 where a ballast 901 is shown separated from housing 902. Ballast 901 may include electronics to limit a current through an electrical load and/or electronics that power and operate the UV light source(s) (not shown). In one embodiment, system 900 can be used as a ceiling mounted disinfection system, where ballast 901 is mounted to or within a ceiling (not shown) and housing 902 can be suspended from ballast 901 by supports 903.

Examples

Figure 10:
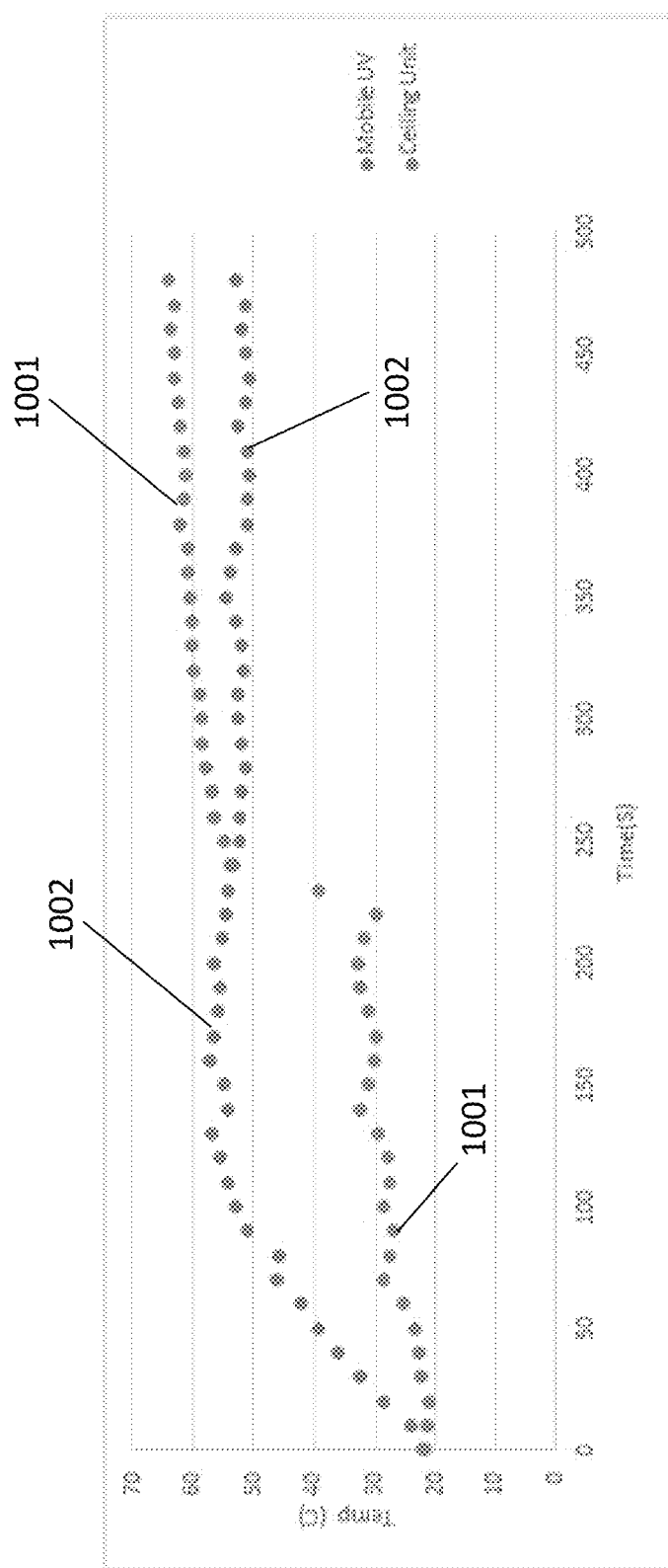
FIG. 10 is a graph showing temperature of a light source over a period of time for two prior art UV disinfection systems.

FIG. 10 shows a graph of temperature (measured in degrees Celsius) of a UVC light source over time (measured in seconds) for a prior art ceiling mounted disinfection system and a prior art mobile UV disinfection system. As shown in the graph, the temperature 1001 of a UVC light source in a ceiling mounted disinfection system slowly increases from ~20° C. to ~30° C. over the first ~225 seconds after being energized. After ~225 seconds, the temperature 1001 of the UVC light source in the prior art ceiling mounted disinfection system increases dramatically to ~50° C. over the next ~25 seconds and then continues to steadily increase from ~50° C. over the next ~250 seconds to ~65° C. The temperature 1002 of a UVC light source in the prior art mobile UV disinfection system increases steadily from ~20° C. to ~55° C. over the first ~125 seconds after being energized. Therefter, the temperature 1002 of the UVC light source in the prior art mobile disinfection system remains steady at ~55° C. for an additional 350 seconds.

Figure 11:
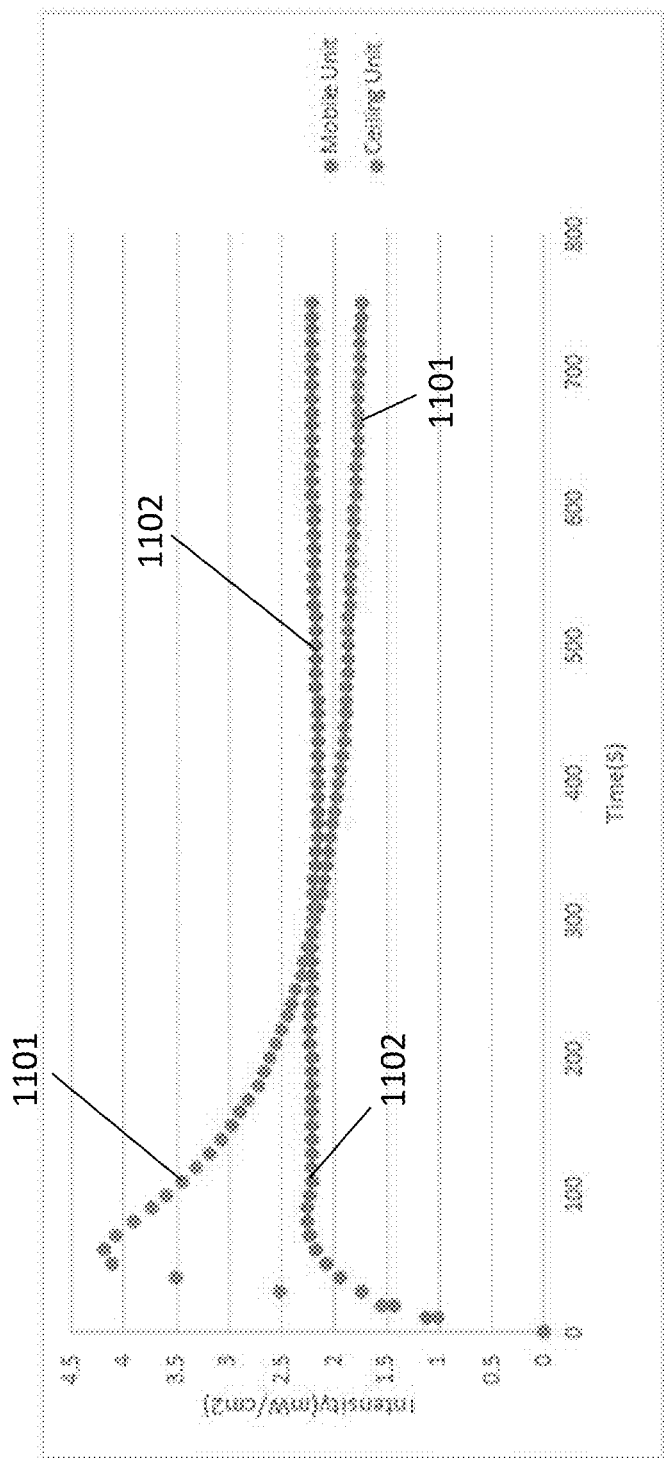
FIG. 11 is a graph showing intensity of a UV light source over a period of time for the two prior art UV disinfection systems used to generate the graph of FIG. 8.

FIG. 11 shows a graph of UVC intensity (measured in milliwatts per square centimeter (mW/cm$^2$) of the UVC light source) over time for the prior art systems used to create FIG. 10. Here, is it shown that the intensity 1101 of the UVC light source in the ceiling mounted disinfection system experiences an initial spike from 0 to ~4.25 mW/cm$^2$ from a time 0 to 50 seconds after being energized. Following this, the intensity 1101 of the UVC light source in the ceiling mounted disinfection system steadily decreases from ~4.25 mW/cm$^2$ to ~1.75 mW/cm$^2$ over the next ~700 seconds. The intensity 1102 of the UVC light source in the prior art mobile UV disinfection system increases steadily from 0 to ~2.25 mW/cm$^2$ over the first ~75 seconds after being energized. Therefter, the intensity 1102 of the UVC light source in the prior art mobile disinfection system remains steady at ~2.25 mW/cm$^2$ for an additional 675 seconds.

Figure 12:
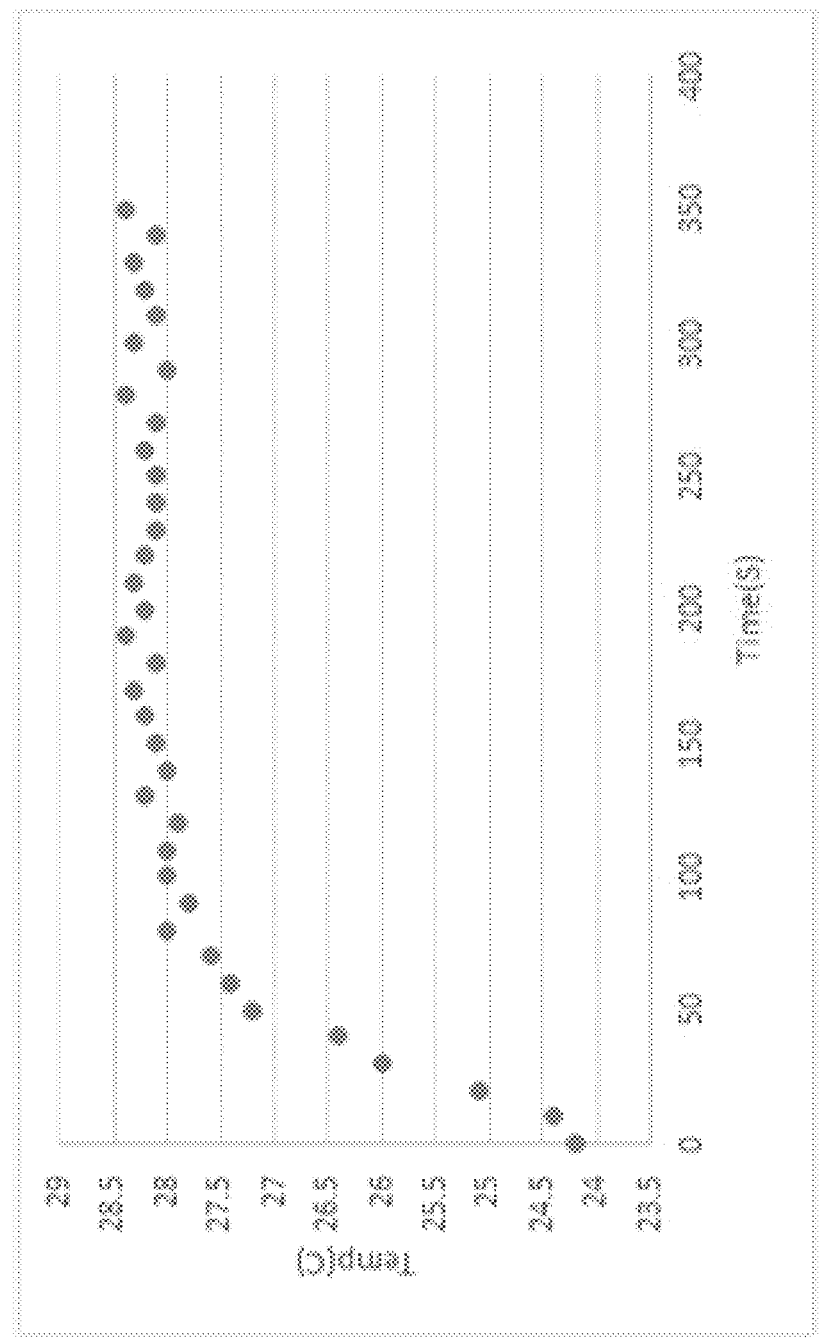
FIG. 12 is a graph showing temperature of a UV light source over a period of time for a UV disinfection system according to one of the embodiments described herein.

FIG. 12 shows a graph of temperature (measured in degrees Celsius (° C.)) of a UVC light source over time (measured in seconds) for a UV disinfection system according to one of the embodiments described herein. As shown in the graph, the temperature of a UVC light source of a UV disinfection system according to one of the embodiments described herein initially increases from ~24° C. to ~28° C. after being energized in a manner similar to the prior art system shown in FIG. 10. However, the temperature of a UVC light source a UV disinfection system according to one of the embodiments described herein does not experience the dramatic increase to ~50° C. approximately 225 seconds after being energized as occurs in the prior art ceiling mounted disinfection system. Rather, as shown in FIG. 12, the temperature of the UVC light source of the UV disinfection system according to one of the embodiments described herein stabilizes at ~28° C. approximately 100 seconds after being energized and remains at ~28° C. for at least another ~250 seconds after reaching ~28° C.

Figure 13:
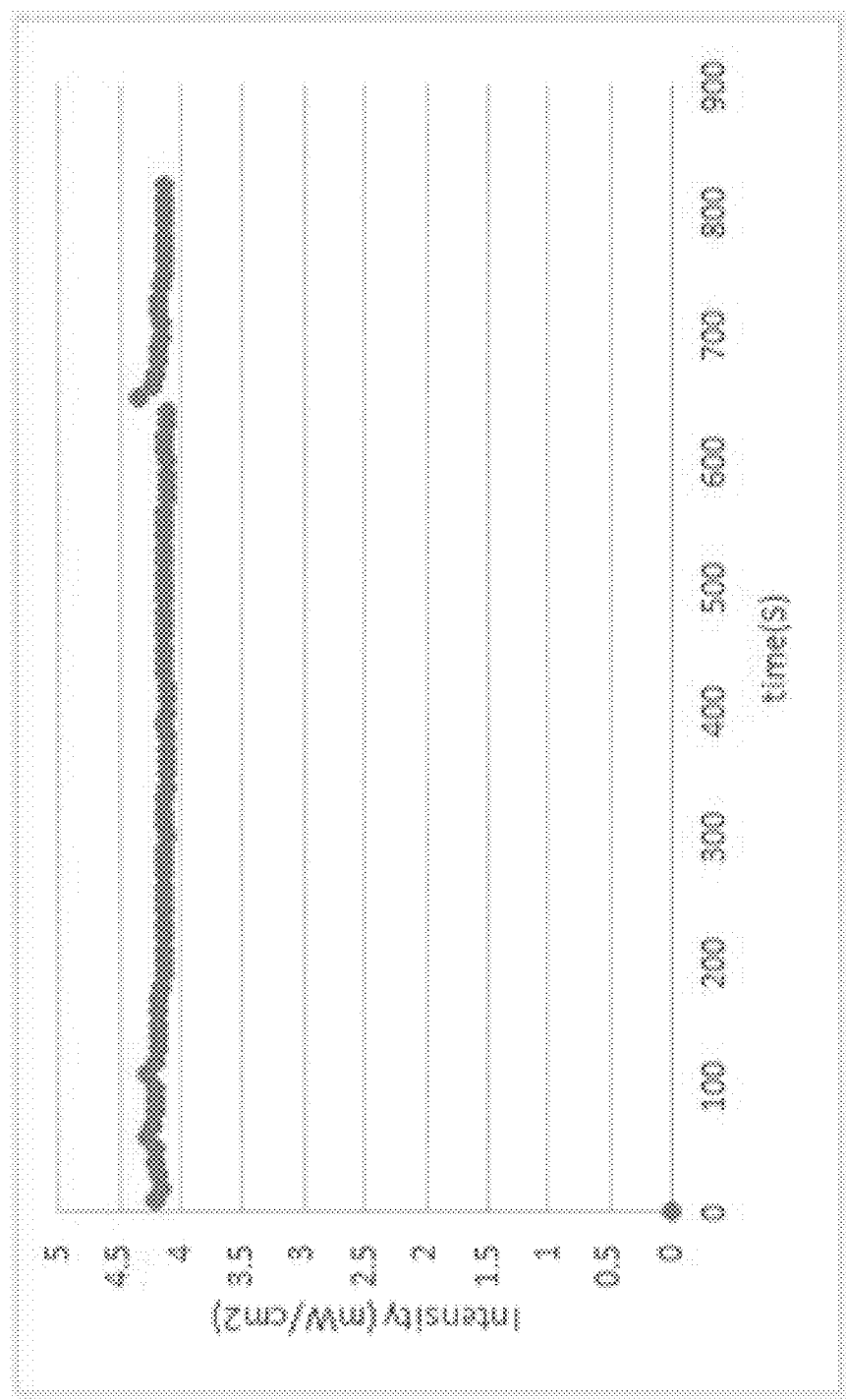
FIG. 13 is a graph showing intensity of a UV light source measured near a surface of a UV light source over a period of time for the UV disinfection system used to generate the graph of FIG. 10.

FIG. 13 shows a graph of UVC intensity (measured in milliwatts per square centimeter (mW/cm$^2$)) of a UVC light source over time for the UV disinfection system used to generate the graph of FIG. 12. Here, it is shown that the intensity of the UVC light source increases to ~4.25 mW/cm$^2$ very quickly after being energized. However, in contrast to the prior art systems shown in FIG. 11, the intensity of the UVC light source of the UV disinfection system according to one of the embodiments described herein is maintained at ~4.25 mW/cm$^2$ at least 800 seconds after being energized. Accordingly, the UVC light source of the UV disinfection system according to one of the embodiments described herein does not decrease in the same manner as the prior art systems used to provide the graph shown in FIG. 11.

Figure 14:
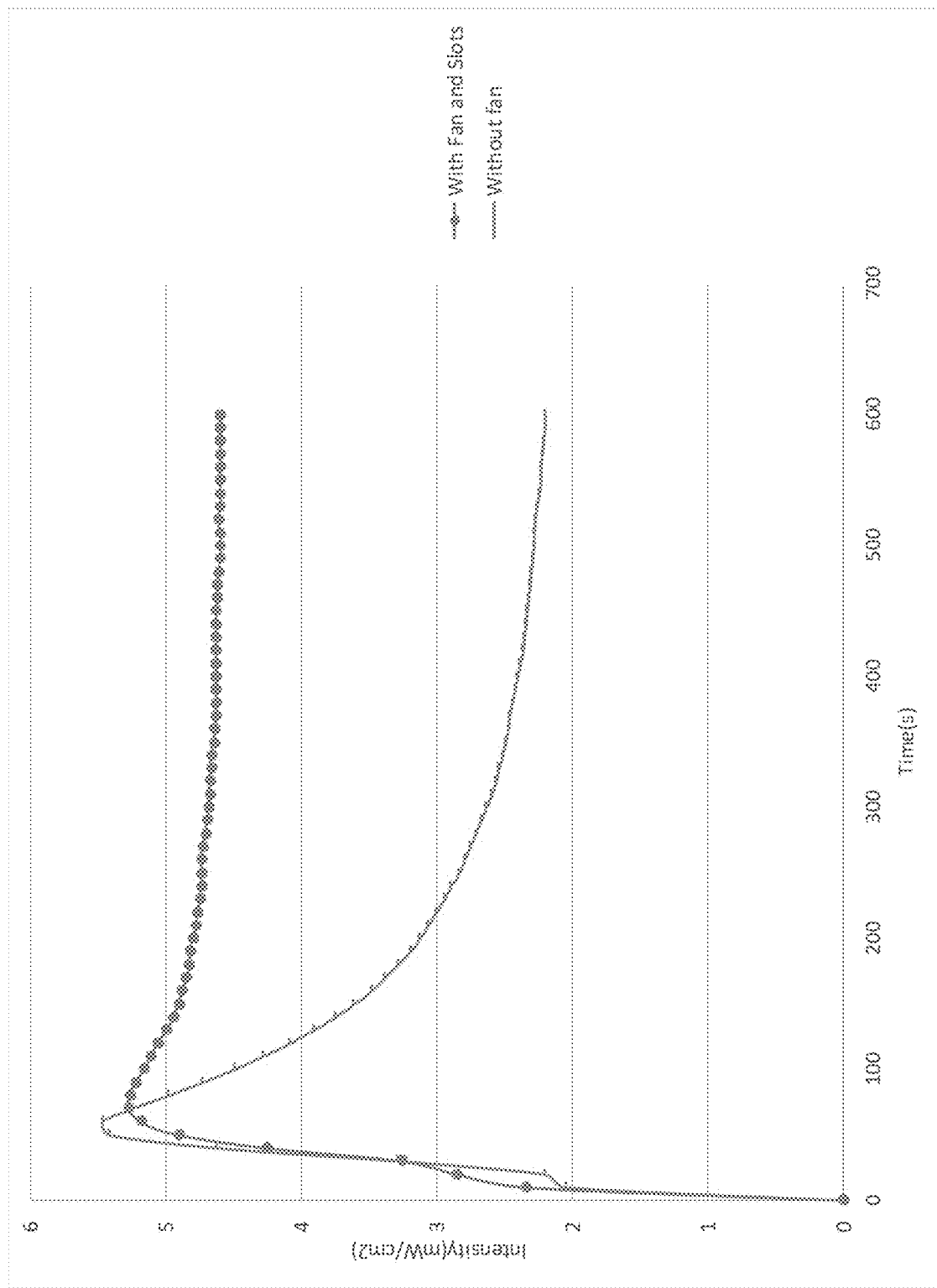
FIG. 14 is a graph showing intensity of a UV light source measured a distance of 8 cm from the UV disinfection system over a period of time for a UV disinfection system incorporating a fan according to one of the embodiments described herein and for a UV disinfection system not incorporating a fan.

FIG. 14 shows a graph showing intensity of a UV light source measured a distance of 8 cm from the UV disinfection system over a period of time for a UV disinfection system incorporating a fan and slots according to one of the embodiments described herein and for a UV disinfection system not incorporating a fan. Here, it is shown that the intensity of UV light as measured at a distance 8 cm from the UV disinfection system according to one of the embodiments described herein slowly declines over time from ~5 mW/cm$^2$ to ~4.5 mW/cm$^2$ between ~100 and ~600 seconds after energizing the light source. This slow decline follows a rapid increase in UV intensity as measured at a distance 8 cm from the UV disinfection system according to one of the embodiments described herein from 0 mW/cm$^2$ to ~5 mW/cm$^2$ between a time 0 (e.g. the time the UV light source was energized) and 100 seconds thereafter.

In contrast, the intensity of UV light as measured at a distance 8 cm from the UV disinfection system without a fan declines more rapidly over time from ~5 mW/cm$^2$ to ~2 mW/cm$^2$ between ~100 and ~600 seconds after energizing the light source. This rapid decline follows a rapid increase in UV intensity as measured at a distance 8 cm from the UV disinfection system without a fan from 0 mW/cm$^2$ to ~5 mW/cm$^2$ between a time 0 (e.g. the time the UV light source was energized) and 100 seconds thereafter. Therefore, the intensity of UV light from a UV light source can be maintained at a much higher level over time using a disinfection system with a fan and slots according to one of the embodiments described herein when compared with a disinfection system that does not include a fan with slots.

Figure 15:
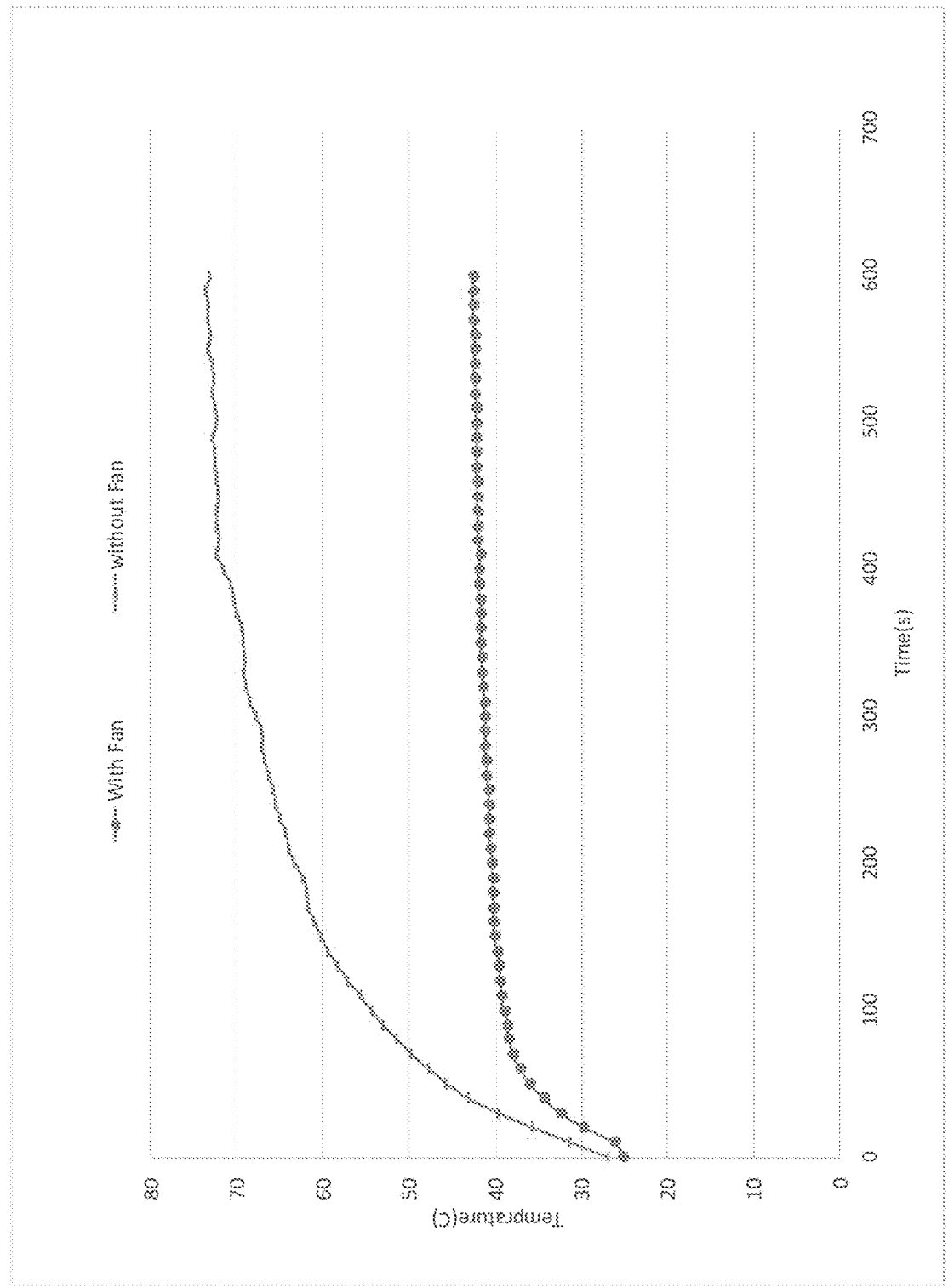
FIG. 15 is a graph showing temperature of a UV light source measured at a surface of the UV light source over a period of time for a UV disinfection system incorporating a fan according to one of the embodiments described herein and for a UV disinfection system not incorporating a fan.

FIG. 15 shows a graph showing temperature of a UV light source measured at a surface of the UV light source over a period of time for a UV disinfection system incorporating a fan according to one of the embodiments described herein and for a UV disinfection system not incorporating a fan. Here, it is shown that the temperature of a UV light source as measured at a surface of the UV light source for a UV disinfection system incorporating a fan according to one of the embodiments described herein slowly increases over time from ~38° C. to ~42° C. between ~100 and ~600 seconds after energizing the light source. This slow decline follows a rapid increase in temperature as measured at a surface of the UV light source for a UV disinfection system incorporating a fan according to one of the embodiments described herein from ~25° C. to ~38° C. between a time 0 (e.g. the time the UV light source was energized) and 100 seconds thereafter.

In contrast, the temperature of a UV light source as measured at a surface of the UV light source for a UV disinfection system not incorporating a fan steadily increases over time from ~25° C. to ~75° C. between a time 0 (e.g. the time the UV light source was energized) and 600 seconds thereafter. Therefore, the temperature of a UV light source can be maintained at a much lower level over time using a disinfection system with a fan according to one of the embodiments described herein when compared with a disinfection system that does not include a fan.

While the above description provides examples of one or more methods or systems, it will be appreciated that other methods or systems may be within the scope of the claims as interpreted by one of skill in the art.

What is claimed is:

1. A disinfection system comprising:
   an UV light source to generate UV light; and
   a housing supporting the UV light source, the housing comprising:
      a fan positioned within the housing to pull air from outside the housing to be directed towards the UV light source; and
      a shield having a body partially surrounding the UV light source and a channel extending along a length of the body, the body having:
         an inner surface sized and shaped to reflect the UV light from the UV light source;
         the body defining a plurality of holes configured to receive air flow from the fan and direct the air flow to contact the UV light source to control a temperature of the UV light source;
      wherein the channel is positioned above the UV light source,
      wherein the plurality of holes is positioned above the UV light source and comprises at least two rows of holes positioned along the length of the body at a predetermined distance from the channel and wherein the at least two rows of holes direct the air flow towards the UV light source at various positions along a length of the UV light source, and
      wherein each of the at least two rows of holes are positioned on a different side of the channel.

2. The disinfection system of claim 1, wherein the inner surface of the shield is sized and shaped to reflect the UV light from the UV light source in a direction away from the housing.

3. The disinfection system of claim 1, wherein the body of the shield is an elongate member.

4. The disinfection system of claim 1, wherein the body of the shield is curved.

5. The disinfection system of claim 1, wherein the body of the shield is semi-circular.

6. The disinfection system of claim 1, wherein at least one hole includes at least one slot.

7. The disinfection system of claim 1, wherein the plurality of holes include slots.

8. The disinfection system of claim 7, wherein the plurality of holes are spaced along the length of the body.

9. The disinfection system of claim 1, wherein the body is made of aluminum.

10. The disinfection system of claim 1, wherein the inner surface is made of aluminum.

11. A housing to support an UV light source, the housing comprising:
    a fan positioned within the housing to pull air from outside the housing to be directed towards the UV light source; and
    a shield fluidly coupled to the fan; the shield having a body partially surrounding the UV light source and a channel extending along a length of the body, the body having:
       an inner surface sized and shaped to reflect UV light from the UV light source through an opening;
       the body defining a plurality of holes configured to receive air flow from the fan and direct the air flow to impinge the UV light source to control a temperature of the UV light source;
    wherein the channel is positioned above the UV light source,
    wherein the plurality of holes is positioned above the UV light source and comprises at least two rows of holes positioned along the length of the body at a predetermined distance from the channel and wherein the at least two rows of holes direct the air flow towards the UV light source at various positions along a length of the UV light source, and
    wherein each of the at least two rows of holes are positioned on a different side of the channel.

12. The housing of claim 11, wherein the inner surface of the shield is sized and shaped to reflect the UV light from the UV light source in a direction away from the housing.

13. The housing of claim 11, wherein the body of the shield is an elongate member.

14. The housing of claim 11, wherein the body of the shield is curved.

15. The housing of claim 1, wherein the body of the shield is semi-circular.

16. The housing of claim 1, wherein at least one hole includes at least one slot.

* * * * *